United States Patent [19]

Adema et al.

[11] 4,014,952
[45] Mar. 29, 1977

[54] PROCESS FOR THE PREPARATION OF ISOPRENE

[75] Inventors: Eduard H. Adema, Geleen; Albert A. Van Geenen, Brunssum; Marinus J. A. M. Den Otter, Munstergeleen, all of Netherlands

[73] Assignee: Stamicarbon B.V., Geleen, Netherlands

[22] Filed: July 15, 1975

[21] Appl. No.: 596,096

[30] Foreign Application Priority Data

July 22, 1974 Netherlands ............... 7409855

[52] U.S. Cl. ............................................. 260/681
[51] Int. Cl.² ...................................... C07C 1/20
[58] Field of Search ............................... 260/681

[56] References Cited

UNITED STATES PATENTS

| 3,754,049 | 8/1973 | Ogino et al. | 260/681 |
| 3,890,404 | 6/1975 | Takagi et al. | 260/681 |

FOREIGN PATENTS OR APPLICATIONS

| 183,737 | 1/1966 | U.S.S.R. | 260/681 |

*Primary Examiner*—C. Davis
*Attorney, Agent, or Firm*—Cushman, Darby & Cushman

[57] ABSTRACT

Preparation of isoprene by conversion of isobutylene or an isobutylene-containing composition with formaldehyde in the gas phase, according to a one-step method, at temperatures of 150° – 400° C, and in the presence of a catalyst.

6 Claims, No Drawings

PROCESS FOR THE PREPARATION OF ISOPRENE

The invention relates to a process for the preparation of isoprene by conversion of isobutylene or an isobutylene-containing composition with formaldehyde in the gas phase, according to a one-step method, at temperatures of 150° – 400° C, and in the presence of a catalyst.

A large number of realizations of such a process are known, e.g. from the British Pat. Specifications Nos. 826,545; 863,330; 841,746; 841,748 and 1,255,578, and from the Dutch Pat. application No. 7,109,621 laid open for inspection. These patent publications mention various catalyst systems, e.g. iso-polyacids or heteropolyacids of Mo, W or V, or acid catalysts based on silica and antimony oxide, or based on silica and bismuth, whether or not mixed with other components, or phosphoric acid, or phosphates of group IIIB elements (boron, aluminum, gallium, etc.).

However, so far the synthesis has not proceeded to full satisfaction. With some catalysts, relatively low conversions are obtained or a large amount of undesirable side products is formed. Others allow of obtaining better conversions, but in most cases the life of such a catalyst is short. The activity of the catalyst decreases rather rapidly, and after a short time the catalyst needs to be regenerated. Although this regeneration can raise the activity of the catalyst considerably, the original activity level is not reached again in many cases. This effect proves to be repetitive, i.e. after every new regeneration the catalyst activity is lower than after the previous one. This means that the catalyst has to be replaced after a comparatively short time.

Now a process has been found in which use is made of a catalyst that regains its original activity after a regeneration at a relatively low temperature, so that it can be used for a long time.

The process according to the invention is characterized in that the catalyst used is copper phosphate on a carrier. This carrier may be one of the carriers normally used, e.g. silica or alumina.

The term 'copper phosphate' as used here refers to compounds that can be obtained from copper oxide or copper hydroxide and a phosphoric acid. By 'phosphoric acid' is meant here any of those acids in which phosphorus may be considered to be pentavalent or which can be imagined to be derived from phosphorus pentoxide. The composition of the products indicated as copper phosphate may deviate from the stoichiometric composition of the copper salts of, for instance, orthophosphoric acid, metaphosphoric acid, and pyrophosphoric acid. Preferably, use is made of a catalyst having an atomic Cu/P ratio of between 10 : 1 and 0.1 : 1, by preference 4 : 1 to 0.25 : 1.

The catalyst can be prepared in various ways, for instance by precipitating copper oxide or copper hydroxide on the carrier and next adding phosphoric acid. According to another method, copper phosphate is suspended in water glass and subsequently gelation with acid is applied. Catalyst preparation is not restricted to these methods. Use may be made of any method suitable for preparing a composition containing one or more copper compounds and one or more phosphoric acids, for instance, conversion of phosphoric acid with a copper salt of a volatile acid.

The isoprene synthesis is effected at temperatures between 150° and 400° C, preferably at a temperature between 225° and 325° C.

The reaction can be carried out at atmospheric pressure, decreased or elevated pressure, in general at pressures of 0.5 to 20 atmospheres.

The ratio between the reaction components can vary within rather wide limits. In general, an excess amount of isobutylene will be used. Preferably, use is made of a reaction mixture containing 1.5 to 3 moles to isobutylene per mole of formaldehyde, although there is no objection to using a greater molar excess of isobutylene.

If the activity of the catalyst declines, it can be raised again by means of a simple regeneration. Preferably the catalyst is regenerated by a treatment with air at a temperature more or less equal to the reaction temperature. As a result of exothermic reactions taking place during the regeneration, the temperature of the catalyst will then rise above the reaction temperature.

In the course of time, and after a number of regenerating treatments at approximately the reaction temperature, the activity is yet found to decrease slightly in some cases.

Surprisingly, it has now been found that if the catalyst in question is then regenerated at higher temperatures, e.g. 400° C or over, the activity can be restored to its original level or virtually to this level. The catalyst can be used much longer than the catalysts known so far, so that it does not need to be frequently replaced.

The formaldehyde used for the conversion with isobutyelene is advantageously obtained from a 10 – 15% aqueous solution, which usually contains some methanol. Of course, other formaldehyde sources may also be used, for instance paraformaldehyde, which is converted into formaldehyde by depolymerization, in a way known in itself.

If use is made of an aqueous formaldehyde solution this is first evaporated and the vapour mixture is mixed with the isobutylene, after which the whole is passed over the catalyst. The water vapour in the reaction mixture then acts as a diluent. If so desired, other diluents may be used as well, such as nitrogen, carbon dioxide, or lower hydrocarbons. The amounts of inert diluent can vary within wide limits and may rise, for instance, to about 95% vol. The diluent may also be formed by other $C_4$ hydrocarbons, if the process is started from a $C_4$-fraction not containing any polyunsaturated compounds and often not containing more than about 50% isobutylene. Surprisingly, it is found that the yield of isoprene is about equally high as it is if pure isobutylene is used, which means that, calculated to isobutylene, the yield is doubled. In this respect the catalyst according to the invention differs very favourably from other known catalysts.

The space velocity of the reaction components can likewise vary widely; in general it is between 0.1 and 50 moles of formaldehyde per liter of catalyst and per hour. The optimum value will depend on the reaction temperature and the activity of the catalyst, and can be easily established by those, skilled in the art. By preference higher space velocities are applied at higher temperatures, and the reverse.

The process of the invention can be realized by the use of known methods for carrying out heterogeously catalyzed gas-phase reactions. The catalyst may be in the form of a fixed or a moving bed, or also a fluidized bed.

The isoprene can be isolated from the conversion product in any suitable manner, for instance by condensation followed by fractional distillation.

Non-converted isobutylene and formaldehyde can be recycled after all or part of the other components of the reaction mixture have been separated out.

The invention will be further elucidated by means of the following examples, without being restricted thereby.

EXAMPLE I 130 grams of sodium silicate was dissolved in 780 ml of distilled water. Subsequently, 17 g of copper(II)-phosphate powder was added, after which the suspension was stirred whilst so much 12-N sulphuric acid was added that the pH of the suspension was 5. The mixture was heated for 3 hours at 100° C, and next kept at room temperature for 24 hours. The gel that had formed was cut up to cubes with edges of about 2 cm. These were washed with water until free of sulphate, dried at 105° C, next crushed and sieved to a size of 0.86 – 3.4 mm. An amount of 17 grams of the catalyst prepared in this way was introduced into a tubular reactor. Next, isobutylene and gaseous formaldehyde were passed over this catalyst at 300° C, at the rates of 0.87 mole/h and 0.15 mole/h. respectively. The formaldehyde was obtained by evaporation of a 20% formaldehyde solution. The quantity of isoprene formed and the degree of isobutylene conversion were determined by gas-chromatographic analysis. The amount of non-converted formaldehyde was determined by collection of sodium sulphite and titration of the sodium hydroxide formed.

From the values found in this way it appeared that in the 2nd to 4th hours of the experiment the selectivity in the conversion into isoprene was 75% for isobutylene and 65% for formaldehyde.

When the experiment was continued, the activity of the catalyst decreased slowly; after about 36 hours it has fallen to 20% of the original activity.

After 36 hours, air was passed over the catalyst at 300° C for 5 hours, which burned away the organic contaminants that had deposited on the catalyst. During this treatment, the temperature of the catalyst bed first rose to 500° C and then dropped again to 300° C. Thereafter, isobutylene and formaldehyde were passed over the catalyst again. The activity of the regenerated catalyst was found to be equal to that of the fresh catalyst.

EXAMPLE II

A solution of 241.6 grams of $Cu(NO_3)_2 \cdot 3H_2O$ in 2 liters of water and a solution of 80 grams of sodium hydroxide in 1 liter of water, were transferred dropwise and with stirring into 1 liter of water, in such a way that the pH was kept at 8.0 to 8.2. The resulting copper(II)-hydroxide was removed by filtration and washed with water until free of nitrate, and then dissolved in 1.6 liters of (25%)ammonia, ammonium carbonate being added to raise the concentration of ammonium ions so as to ensure complete dissolution. Thereafter 500 grams of Aerosil 200 was added and the mixture was boiled. In this treatment ammonia escaped and the cupric oxide was precipitated on the carrier. After boiling for 24 hours the precipitate was removed by filtration, washed with water until free of $NH_4$, and dried for 24 hours at 120° C.

The product was pelleted to pellets having a height of 3 millimeters and a diameter of 5 millimeters; it contained 8.8% Cu and 79.1% $SiO_2$.

A quantity of 31.7 grams of these pellets (44 millimoles of cupric hydroxide) was steeped to capacity in 20 milliliters of water with 15 millimoles of phosphoric acid, and subsequently dried in a drying furnace at 105° C.

12.5 grams (25 milliliters) of this catalyst was calcined under an air stream in a tubular reactor for 4 hours at 400° C. After cooling to 250° C under nitrogen, isobutylene and gaseous formaldehyde were passed over the catalyst at the rates of 0.45 mole/h and 0.15 mole/h, respectively. The formaldehyde had been obtained by evaporation of a 37% solution containing 8% methanol. After 4 hours the reactor was flushed with nitrogen for 5 minutes and next air was passed over the catalyst bed for 4 hours so as to burn away the organic contaminants. During this treatment the temperature of the bed rose to about 400° C, to drop to 250° C after another 4 hours. After a new flushing with nitrogen for 5 minutes, the same mixture of reactants was passed through. This procedure was repeated several times. The measurements were performed in in the same way as described in Example I. It was found that in the first 4 hours the selectivity with which isobutylene was converted into isoprene amounted to 70%. After 340 hours the activity of the catalyst had dropped to 40% of its original value.

By regenerating with air for 15 hours, starting at a temperature of 400° C, a catalyst was obtained which has the same activity as the fresh catalyst.

EXAMPLE III 12.5 grams of catalyst was calcined at 400° C under air in a tubular reactor for 4 hours and subsequently cooled to 250° C under nitrogen. The catalyst had been prepared in the way described in example II, but this time with such an amount of phosphoric acid that the atomic copper/phosphorus ratio was 0.5. Isobutylene and gaseous formaldehyde were passed over this catalyst at the rates of 0.45 mole/h and 0.15 mole/h, respectively, the formaldehyde having been obtained by evaporation of a 37% formaldehyde solution. The measurements were carried out as described in example I. They showed isobutylene to have been converted into isoprene with a selectivity of 70% in the first 2 hours.

EXAMPLE IV

In the same way as described in Example II, isobutylene and formaldehyde were passed, at the respective rates of 0.45 mole/h and 0.15 mole/h, over a catalyst prepared by the method described in Example II.

The isobutylene was converted into isoprene with a selectivity of 70%; the yield was 5% with respect to isobutylene. After 24 hours a mixture of a $C_4$ fraction not containing poly-unsaturated compounds, and containing 45% isobutylene, and formaldehyde was passed over the catalyst. The flow rates were 0.25 mole/h for isobutylene and 0.15 mole/h for formaldehyde.

The selectivity was found to be equal to the selectivity in the first 24 hours. The yield was 10% with respect to the isobutylene.

This showed the use of the $C_4$ fraction containing 45% isobutylene resulted in the isoprene yield, with respect to the isobutylene used, being about doubled.

What is claimed is:

1. Process for the preparation of isoprene by conversion of isobutylene or an isobutylene-containing composition with formaldehyde in the gasphase, according to a one-step method, at temperatures of 150° – 400° C, and in the presence of a catalyst, wherein the catalyst used is a copper-phosphate composition on a carrier.

2. Process according to claim 1, wherein the copper-phosphate composition has an atomic Cu/P ratio of between 10 : 1 and 1 : 10.

3. Process according to claim 2, wherein the copper-phosphate composition has an atomic Cu/P ratio of between 4 : 1 and 1 : 4.

4. Process according to claim 1 wherein a catalyst is used which has been prepared by precipitating copper oxide and/or copper hydroxide on the carrier and next reacting it with phosphoric acid.

5. Process according to claim 1, wherein a catalyst is used which has been prepared by suspending copper phosphate in water glass and next gelating with acid.

6. Process according to claim 1, wherein the carrier used is silica.

* * * * *